United States Patent
Hoyns et al.

(10) Patent No.: US 6,766,186 B1
(45) Date of Patent: Jul. 20, 2004

(54) POST BIOSPY TISSUE MARKER AND METHOD OF USE

(75) Inventors: Dirk V. Hoyns, SW. Conyers, GA (US); Terrell A. Pruitt, Lawrenceville, GA (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 09/268,814

(22) Filed: Jun. 16, 1999

(51) Int. Cl.[7] ............................................. A61B 10/00
(52) U.S. Cl. ..................... 600/431; 600/567; 600/167; 606/167
(58) Field of Search ................................ 600/431, 564, 600/567; 128/897, 898; 606/167, 130

(56) References Cited

U.S. PATENT DOCUMENTS

| | | | |
|---|---|---|---|
| 5,221,269 A | | 6/1993 | Miller et al. ................ 604/281 |
| 5,246,011 A | * | 9/1993 | Caillouette .................. 600/566 |
| 6,220,248 B1 | * | 4/2001 | Voegele et al. ............. 128/898 |
| 261,243 A1 | * | 7/2001 | Burney et al. .............. 600/564 |

OTHER PUBLICATIONS

Article—Piper Jaffray Research on Biopsys Medical, Inc., Apr. 18, 1997, p. 3.
Brochure—Advanced Breast Care Technologies for MIBB, three illustrated pages.
Brochure—Biopsys Mammotome Biopsy System, six illustrated pages, 1997.

* cited by examiner

*Primary Examiner*—Ruth S. Smith
(74) *Attorney, Agent, or Firm*—Kilpatrick Stockton LLP

(57) ABSTRACT

An implant for marking a location within the tissue of a patient after biopsy is self-anchoring. In one embodiment a strip of a shape memory alloy such as Nitinol can be straightened to facilitate insertion through a small gauge needle but, once exposed within the tissue to body temperature, assumes a helical coil configuration, thereby mechanically clamping to the tissue. In other embodiments the implants include barbs of resilient, deformable metal which can be straightened for insertion into a small gauge needle, but once the implant exits the forward end of the needle the barbs spring outward, anchoring the implant within the tissue. A method for implanting a plurality of markers within the tissues of a patient involves a needle having a plurality of markers sequentially loaded therewithin. The forward end of the needle is inserted into the tissues of the patient and advanced to a first target location, at which point a first marker is ejected into the tissues of the patient. The forward end of the needle is then relocated to a second target site, and a second marker is ejected into the tissues of the patient.

11 Claims, 6 Drawing Sheets

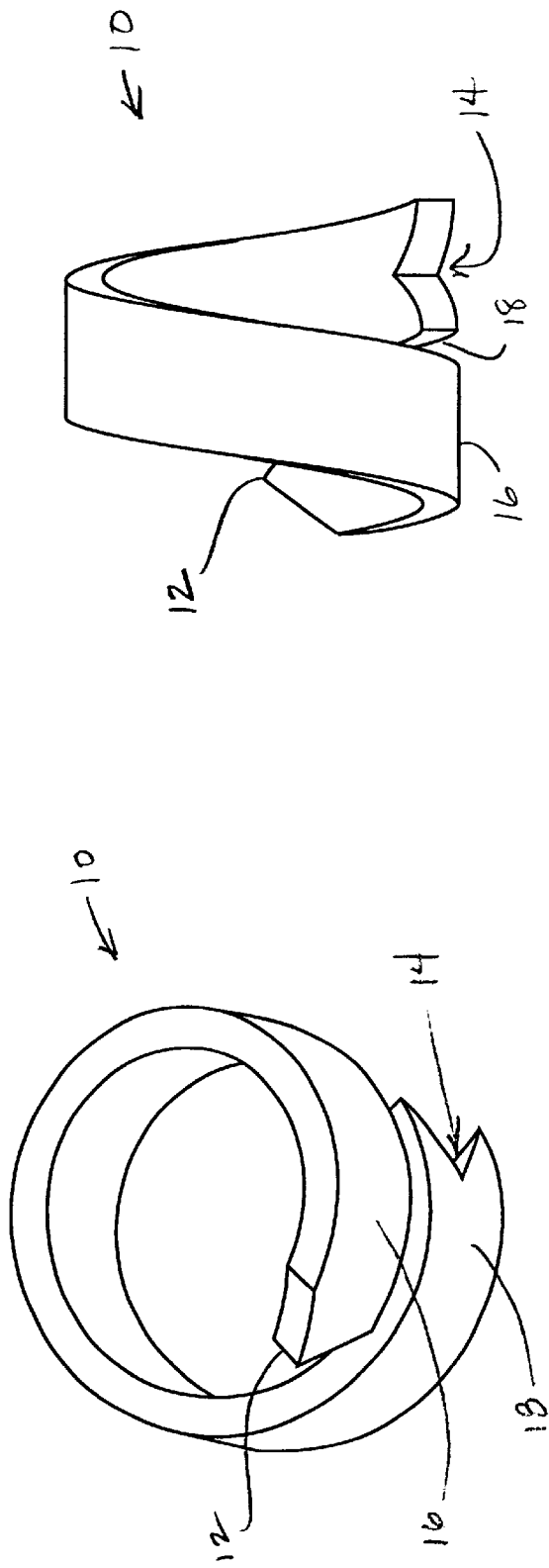
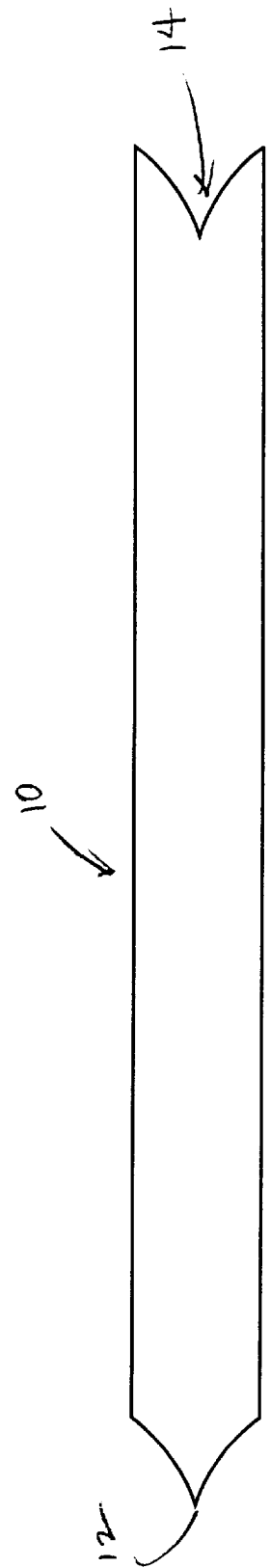

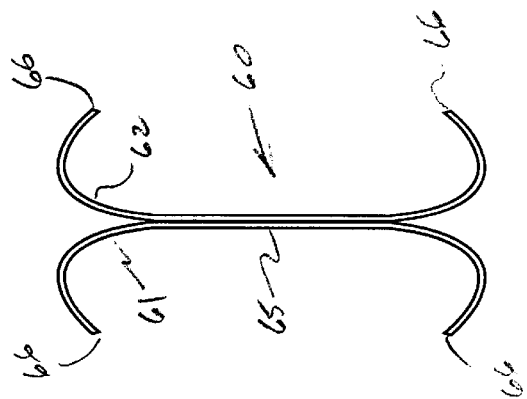
*Fig. 14*
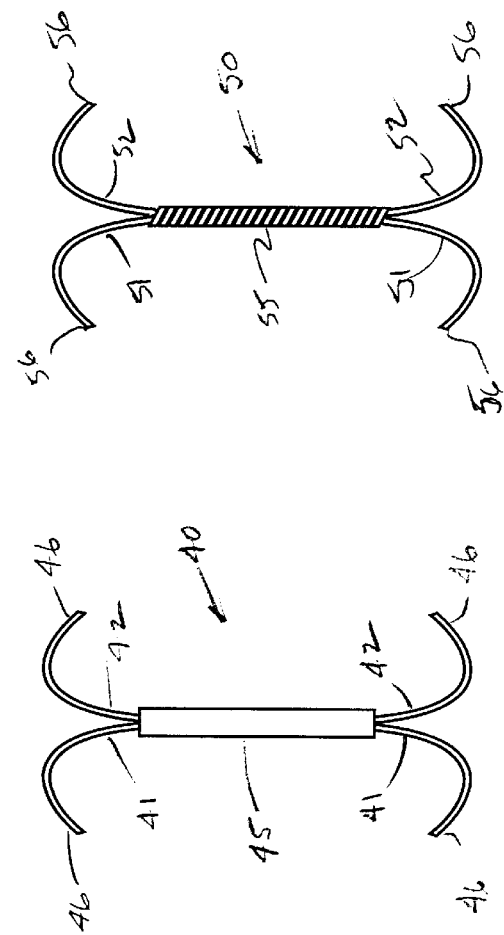
*Fig. 13*
*Fig. 9*
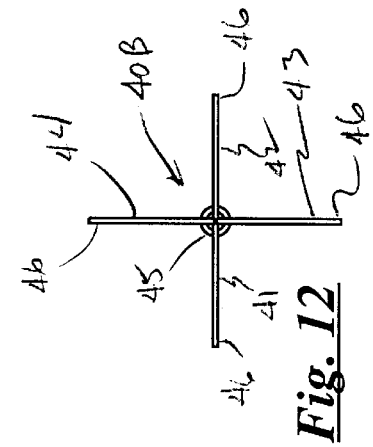
*Fig. 12*
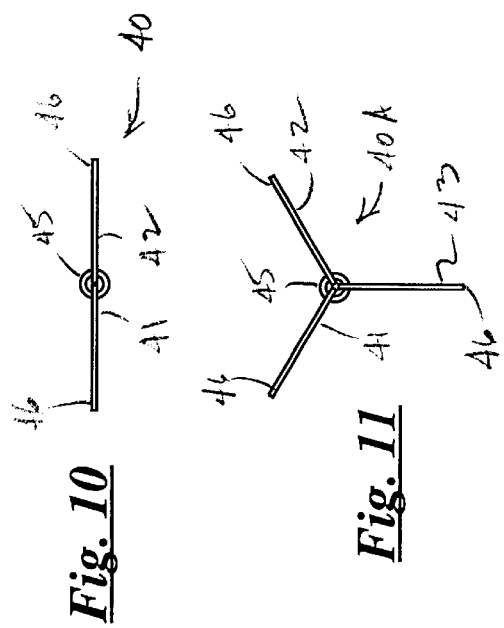
*Fig. 10*
*Fig. 11*

POST BIOSPY TISSUE MARKER AND METHOD OF USE

TECHNICAL FIELD

The present application relates generally to markers for surgically implanting within the tissues of a patient to mark the location of a lesion. More specifically, the present invention relates to a marker which is mechanically self-anchoring within the target tissue and which can be delivered through a relatively small gauge needle.

BACKGROUND OF THE INVENTION

Advances in modern medical imaging technologies such as X-ray, ultrasound, or magnetic resonance imaging make it possible to identify and to biopsy tumors while they are still small. When dealing with a small tumor, especially after a portion of the tumor has been removed for biopsy, it is sometimes difficult to relocate the tumor at a later time for treatment. This is particularly true in the case of tumors in the breast, where the ability to visualize a small growth may depend upon the manner in which the breast is positioned or compressed during the procedure. In addition, prior to surgically removing a tumor, it is often advantageous to try to shrink the tumor by chemotherapy or irradiation. This is especially true in the case of breast cancer, where conservation of breast tissue is a concern. Shrinkage of the tumor can sometimes make it difficult for the surgeon to locate the tumor. It is therefore often desirable to place a marker within the target tissues at the time of biopsy which can be visualized under a variety of imaging modalities to facilitate finding the tumor at a later time.

For such a marker to be effective, it must be visible under a variety of imaging modalities and must maintain its position within the tissues. Implants placed loose within the tissues have a tendency to migrate, and this tendency is particularly acute in the case of fatty tissue, such as the breast. Accordingly, for such a marker to resist migration, it must clamp or otherwise attach to the target tissues. One device which is currently being used is implanted into the target tissues and then manipulated remotely by means of wires to cause the implant to clamp to the target tissue. However, the manipulation of the wires to clamp the device to the target tissues complicates the deployment procedure. Further, it is possible that the wire may not properly detach from the implant.

Another device which is currently in use involves a C-shaped or U-shaped marker which is implanted and then crimped with a pliers-like instrument to attach the marker to the tissue. However, this process also requires affirmative intervention by the physician beyond simply guiding the marker to the desired location, namely, the step of crimping the marker to anchor it to the tissues. Thus, there is a need for a marker which automatically mechanically attaches to the target tissues upon being deployed, without the need for intervention by the surgeon.

Because of advances in biopsy technology, it is possible to biopsy suspicious tissue with a fourteen or even sixteen gauge or smaller needle. Use of such a small gauge needle minimizes patient discomfort and makes it possible to retrieve the biopsy specimen through a small incision. Since a marker which can be implanted only through a larger needle or incision, or which would require a larger instrument to crimp the anchor to the tissues, would largely defeat the advantages of needle biopsy, there is a need for a marker as well as an apparatus and method for implanting the marker which is capable of implanting and anchoring the marker by way of an instrument no larger in diameter than the needle used for biopsy purposes.

SUMMARY OF THE INVENTION

Stated generally, the present invention comprises a marker for implanting in the tissues of a patient, such as at the time of a biopsy, to facilitate locating the site at a future date. The marker is self-anchoring, automatically mechanically attaching to the target tissues upon being deployed without the need for intervention by the, surgeon. The marker is capable of being implanted through a needle no larger than the needle used for biopsy purposes.

Stated somewhat more specifically, the present invention comprises a marker for inserting by a physician through a lumen of a hollow needle to a target site within the tissues of a patient to facilitate locating the target site at a later time. The marker is capable of assuming an essentially linear configuration for passage through the hollow needle. The marker includes means for anchoring itself to the tissues of the patient without intervention by the physician.

In a first aspect the marker is comprised of a shape memory alloy having a phase change temperature which is higher than normal room temperature but lower than the normal body temperature of the patient. When the marker is exposed to a temperature below the phase change temperature, the marker can be configured into an elongated, essentially linear configuration for passage through the needle. When the marker is exposed to a temperature higher than the phase change temperature, such as by exposure within the tissues of the patient, the marker assumes a predetermined configuration which will anchor it to the tissues of the patient without intervention by the physician. According to one embodiment, the marker assumes a helical shape upon being exposed to a temperature higher than its phase change temperature. In another embodiment the marker assumes a ring shape.

In another aspect, the marker is comprised of a plurality of wires whose free ends form barbs. The barbs are normally bent outward but can be deformed into an essentially linear configuration for passage of the marker through a hollow needle. Upon the marker exiting the forward end of the needle the barbs spring outward, anchoring the marker to the tissue. According to one embodiment, two or more wires are anchored within a tubular body portion with their free ends extending from either end of the tubular body portion to form the barbs. In another embodiment, the central portions of two or more wires are twisted together, with the free ends of the wires forming barbs. In yet another embodiment, the central portions of two or more wires are bonded together, such as by welding, adhesives, heat shrink tubing, or other biocompatible method, with the free ends of the wires configured into barbs.

The invention further includes a method for implanting a plurality of markers within the tissues of a patient. A plurality of markers of the type previously described are sequentially loaded into a hollow needle. A stylet is inserted into the rearward end of the hollow needle to push the markers through the needle and out its forward end. According to the method of the invention the forward end of the needle is positioned at a first location, and the stylet is advanced to eject a first marker from the forward end of the needle and into the tissues of the patient. The forward end of the needle is then repositioned to a second location without withdrawing the needle from the patient, and the stylet is further advanced to eject a second marker from the forward end of the needle and into the tissues of the patient.

Thus it is an object of the present invention to provide an improved marker for implanting in the tissues of a patient, such as at the time of a biopsy, to facilitate locating the site at a future date.

It is another object of the present invention to provide a marker which is automatically self-anchoring without the need for intervention by the surgeon.

Still another object of the present invention is to provide a marker which can be visualized under a variety of imaging modalities and yet which can be implanted through a needle no larger than the needle used for biopsy purposes.

Other objects, features, and advantages of the present invention will become apparent upon reading the following specification, when taken in conjunction with the drawings and the appended claims.

BRIEF DESCRIPTION OF THE DRAWINGS

FIG. 1 is a perspective view of a post biopsy tissue marker according to a first embodiment of the invention.

FIG. 2 is an end view of the tissue marker of FIG. 1.

FIG. 3 shows the tissue marker of FIG.1 uncoiled into an essentially straight configuration to facilitate insertion through a cannula.

FIG. 5 shows three of the markers of FIG. 1 loaded within the cannula;

FIG. 6 shows the stylet being advanced to eject the first marker from the forward end of the cannula;

FIG. 7 shows the first marker assuming its helical configuration, the cannula is repositioned, and the stylet is advanced again to eject the second marker; and FIG. 8 shows the first and second markers clamped within the target tissue and spaced apart relation.

FIG. 9 is a side view of a second embodiment of a post biopsy tissue marker according to the present invention.

FIG. 10 is a top view of the tissue marker of FIG. 9.

FIG. 11 is a top view of an alternate version of the tissue marker of FIG. 9.

FIG. 12 is a top view of another alternate version of the tissue marker of FIG. 9.

FIG. 13 is a side view of another alternate embodiment of a tissue marker according to the present invention.

FIG. 14 is a side view of yet another embodiment of tissue marker according to the present invention.

FIG. 15 shows the marker being loaded into the rearward end of a cannula;

FIG. 16 shows the marker assuming an essentially linear configuration as it is advanced into the cannula; and FIG. 17 shows the barbs of the marker springing outward as the marker exits the forward end of the needle to anchor the marker within the tissue.

FIG. 18 is a cutaway view of the apparatus loaded with two markers, with the tip of the apparatus positioned at a first target location within the tissues of a patient;

FIG. 19 shows the actuation of the device to discharge a marker into the tissues of a patient at the first target location;

FIG. 20 shows the relocation of the tip of the device to a second target location; and FIG. 21 shows the actuation of the device to discharge a second marker into the tissues of the patient at the second target location.

DETAILED DESCRIPTION OF THE DISCLOSED EMBODIMENT

Figure 4:
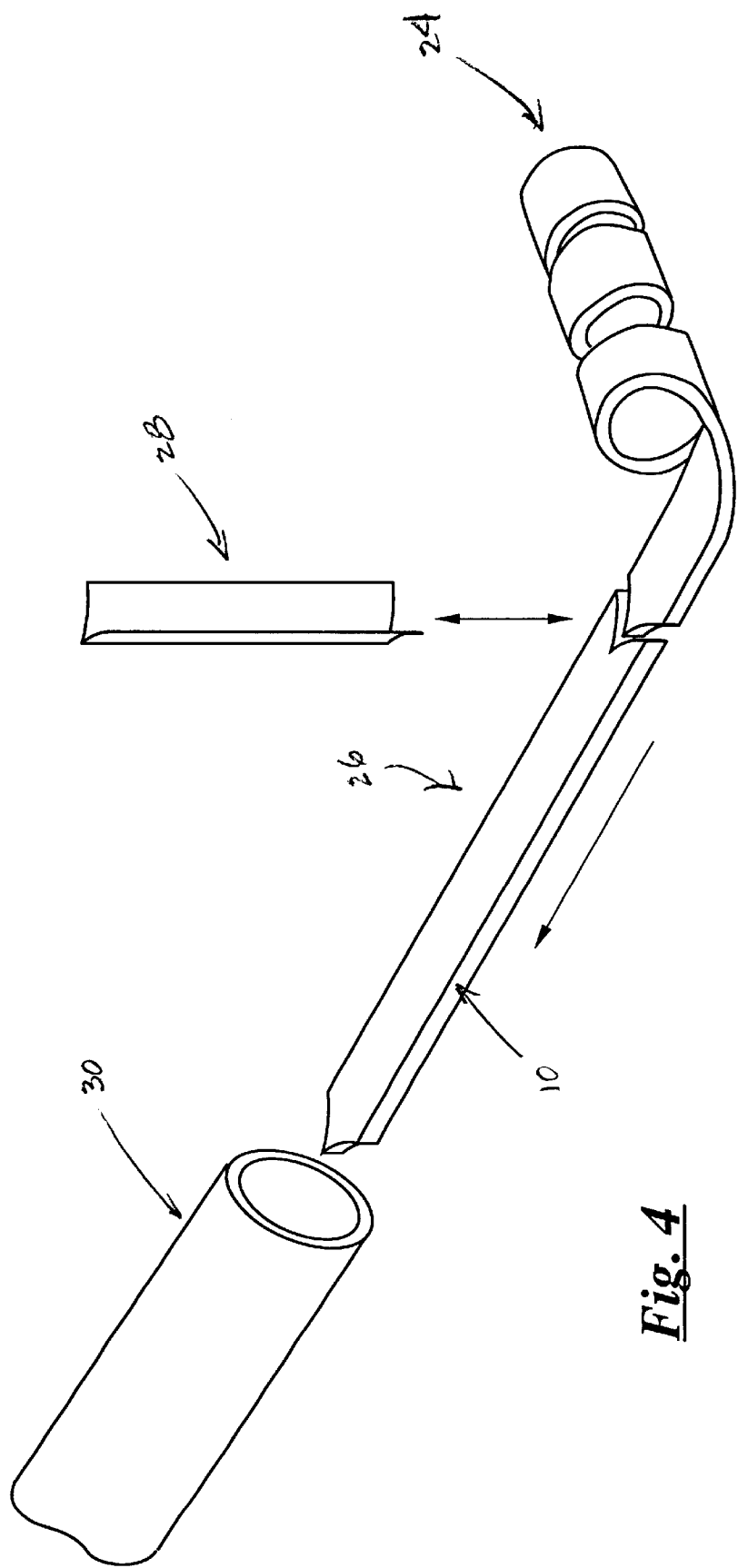
FIG. 4 is schematic representation illustrating the fabrication of the tissue marker of FIG. 1 and the loading of the marker into a hollow cannula.

Referring now to the drawings, in which like numerals indicate like elements throughout the several views, FIGS. 1–3 illustrate a breast marker 10 according to a first embodiment of the invention. The marker 10 is fabricated from a material that has shape memory properties, such as Nitinol or other biocompatible material that allows for a phase change from the martensitic state to austenitic state at a predetermined transformation temperature. The transformation temperature for the preferred embodiment is approximately 37° C. (98.6° F.), which is nominal human body temperature. Below the transformation temperature the implant 10 can be formed into an essentially linear configuration, as shown in FIG. 3, to facilitate implantation through a hollow cannula. When the implant 10 is heated to the transformation temperature, such as by exposure within the tissues of a patient, the implant assumes a helical shape, as shown in FIGS. 1 and 2. This shape memory action causes the marker to be "self-closing" or "self-clamping" without any further intervention by the surgeon.

Another reason for fabricating the marker 10 from Nitinol is that Nitinol is radiopaque, ultrasonically opaque, and MRI compatible, meaning it is visible under magnetic resonance imaging without causing artifacts which can obscure visualization of adjacent tissue.

The marker 10 includes a sharpened point 12 at its forward end and a notch 14 at its rearward end. The sharpened point 12 permits the marker 10 to penetrate the target tissue easily. The notch 14 at the rearward end of the marker serves no particular function but is simply the recess left as a result of a point 12 of a contiguous marker 10 being punched from the same strip of metal.

When the marker 10 is heated to its phase change temperature, it assumes the helical configuration of FIGS. 1 and 2. The helix prescribes an arc of greater than 360° so as to create overlapping portions, 16, 18. The overlapping portions 16, 18 are closely spaced so that when the marker 10 assumes its helical configuration within the target tissue, tissue is clamped between the overlapping portions.

In the disclosed embodiment, the tissue marker in its straightened configuration is 0.250 inches (6.35 mm) long, 0.020 inches (0.5 mm) wide, and 0.006 inches (0.15 mm) thick. In this configuration, the marker fits easily through a sixteen gauge needle. When the marker is in its helical configuration, it has a diameter of approximately 0.060 inches (1.5 mm).

Fabrication of the markers 10 will now be explained with reference to FIG. 4. The markers 10 are fabricated from a helical coil 24 of Nitinol. The manufacturing process takes place at a temperature lower than the phase change temperature of the Nitinol. With the Nitinol in its martensitic phase, the material can be straightened and will essentially maintain the straightened configuration until heated to its phase change temperature. A short length 26 of the end of the coil 24 is straightened and punched with a V-shaped punch 28 to separate a marker 10 from the remainder of the coil.

The V-shaped punch 28 also forms the pointed forward end 12 of the marker 10. The marker 10 is then immediately loaded into the rearward end of a hollow cannula 30. The next section of the coil 24 is then straightened and punched, and the next marker 10 is inserted into the hollow cannula 30 behind the first marker. The markers are not completely straight but retain a slightly bowed configuration, thereby exerting enough interference with the walls of the cannula 30 not to slide freely within the cannula. In the disclosed embodiment, three or four markers 10 are inserted into each cannula 30. A stylet 32 is then inserted into the rearward end of the cannula 30. The markers 10, cannula 30, and stylet 32 are then sterilized and packaged as a unit. The physician thus receives the needle assemblies preloaded with markers, so that the markers never have to be handled once they leave the factory.

Figure 5:
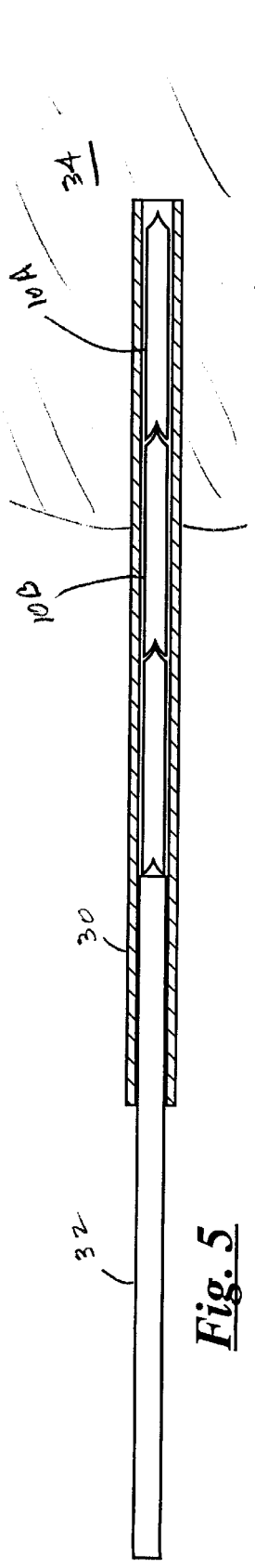
FIGS. 5–8 are schematic representations showing the sequence for implanting the markers of FIG. 1 with a cannula and stylet, with the top half of the cannula removed to reveal interior detail, where.
Figure 6:
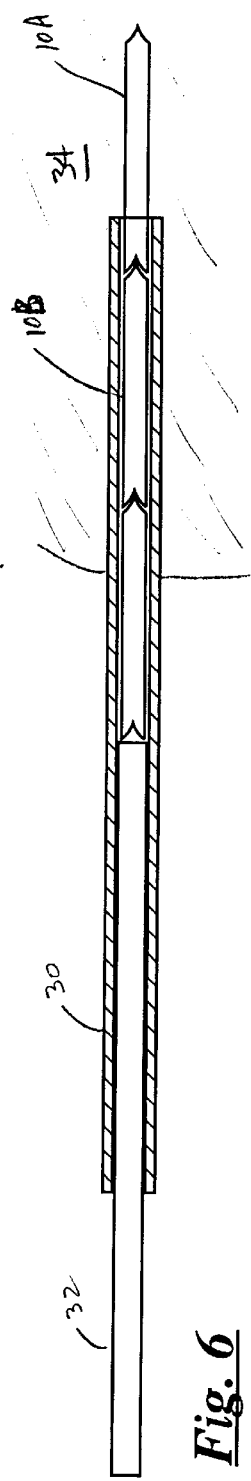
Figure 7:
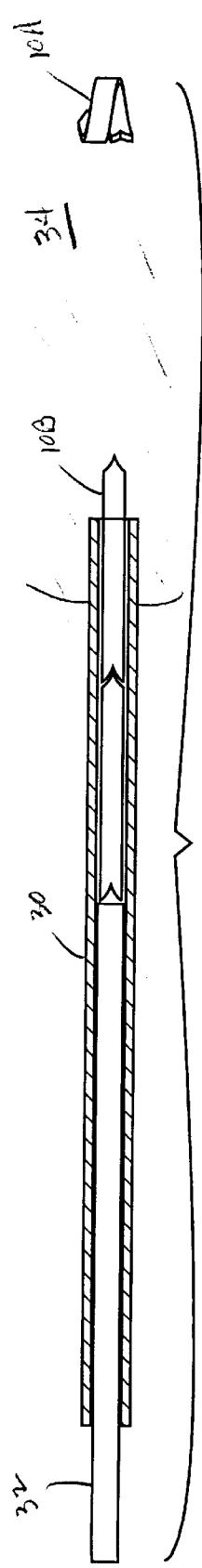
Figure 8:
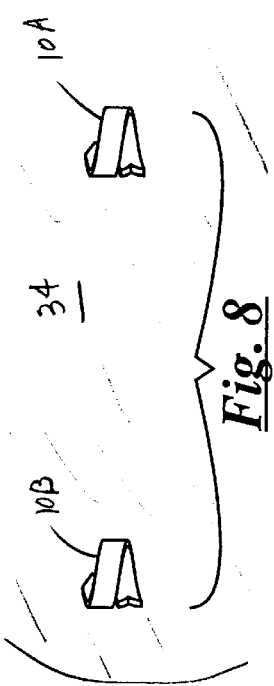

Implantation of the markers will now be discussed with reference to FIGS. 5–8. The physician inserts the forward end of the cannula 30 through the same puncture through which the biopsy was taken and advances the tip of the cannula to a location adjacent to the target tissue 34, as shown in FIG. 5. Then, as shown in FIG. 6, the physician advances the stylet 32, forcing the column of markers 10 forward within the cannula 30 and ejecting the front marker 10A out the forward end of the needle and into the target tissue 34. When exposed to body temperature within the target tissue 34, the marker 10A is heated to its phase change temperature and coils into its helical configuration, thereby clamping itself to the target tissue 34. If deployment of a second marker 10 is required, the physician repositions the tip of the cannula 30 and advances the stylet 32 to eject the second marker 10B from the forward end of the cannula, as shown in FIG. 7. After the desired number of markers 10 have been placed in the appropriate locations, the needle assembly is withdrawn, leaving the markers 10 mechanically attached to the target tissues as shown in FIG. 8.

FIGS. 9–14 show alternate embodiments of self-anchoring markers. Rather than utilizing a shape memory metal which will assume a predetermined configuration upon begin exposed to body temperature within the target tissue, the embodiments of FIGS. 9–14 are anchored by means of resilient barbs, which can be straightened into an essentially linear configuration for passage through a cannula and then spring outward upon exiting the forward end of the cannula to anchor the marker within the target tissues.

Referring to FIGS. 9 and 10, a marker 40 includes a pair of wires 41, 42 which are inserted through a short length of tubing 45. The wires 41, 42 are secured to the tubing 45 by welding, soldering, adhesive bonding, crimping the tubing to clamp the wires, or any other suitable biocompatible means. The exposed ends of the wires 41, 42 are bent outward to form barbs 46. In the disclosed embodiment, the tubing 45 is approximately 0.060 inches (1.5 mm) long and 0.050 inches (1.27 mm) in diameter and is formed from stainless steel or other suitable radiopaque, ultrasonically opaque material. The wires 41, 42 are formed from 0.010 inch (0.25 mm) stainless steel, which is one example of a material which has been shown to exhibit the requisite degree of deformability and resiliency. NiTi has also been found to be a suitable material where MRI compatibility is desirable.

The marker 40 is comprised of two wires, each having two free ends, for a total of four barbs 46. As can be seen in FIG. 10, the barbs 46 are all substantially disposed in a common plane. However, it will be appreciated that a greater number of wires can be incorporated into a marker 40 to provide more barbs 46, and that the barbs can be arranged other than in a common plane. FIG. 11, for example, shows a marker 40A comprising three wires 41, 42, and 43, anchored within a tube 45. Three barbs are formed at each end of the marker 40A and are disposed at 120° intervals. FIG. 12 shows a marker 40B comprising four wires 41–44 anchored within a tubing 45 and forming four barbs 46 at each end of the marker which are disposed at 90° intervals.

FIG. 13 shows a marker 50 comprised of two pieces of wire 51, 52 whose middle portions are twisted together as at 55. The free ends of the wires 51, 52 are bent outward to form barbs 56.

FIG. 14 shows another marker 60 comprised of a pair of wires 61, 62 whose central portions are welded together at 65. The free ends of the wires are bent outward to form barbs 66.

In addition to securing wires within a tubing, twisting wires together, or welding wires together, it will be appreciated that other means for fastening two or more wires together along their intermediate portions can be employed, including but not limited to adhesive bonding, heat shrink tubing, or other suitable biocompatible methods. In addition, while the barbed markers previously described are all fabricated by fastening two or more wires together, it is feasible to fabricate a marker from a single piece of material, for example, an elongated strip which is split at both ends, the middle portion remaining intact while the split ends are bent to form a plurality of barbs.

Figure 17:
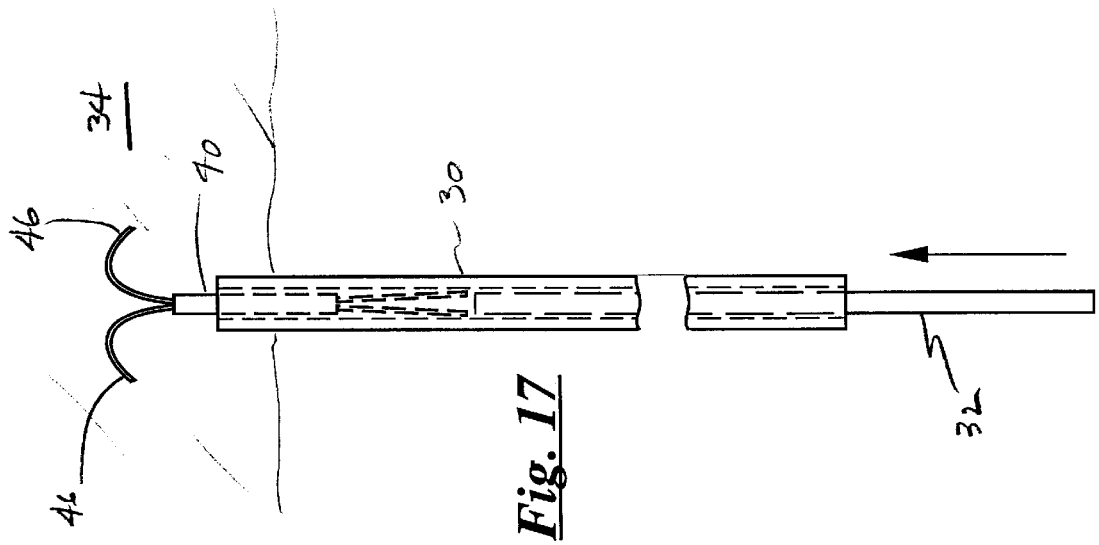
FIGS. 15–17 schematically represent the procedure for implanting the marker of FIG. 9, where.
Figure 16:
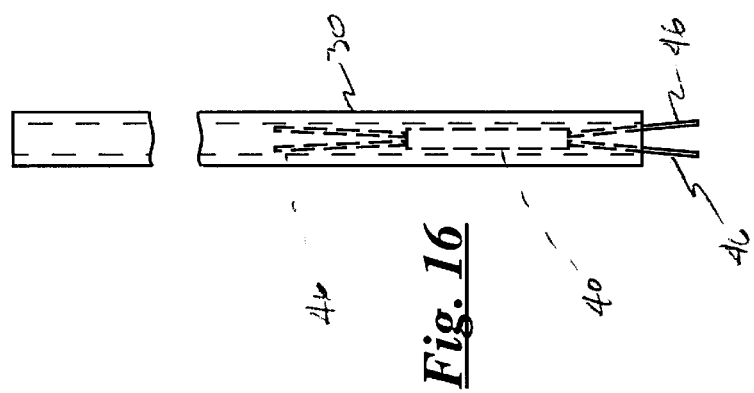
Figure 15:
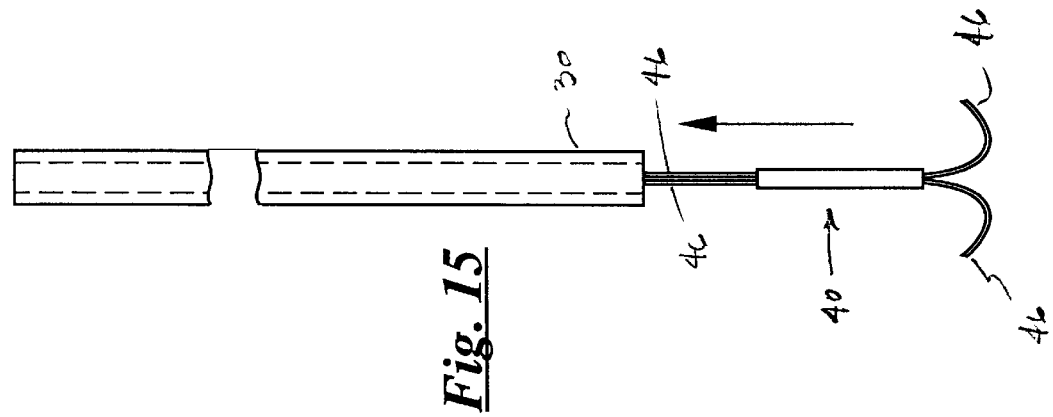

FIGS. 15–17 illustrate the procedure for implanting a barbed-type marker. While the procedure will be demonstrated with respect to a marker 40 in which the wires 41, 42 are fastened together by means of a tubing 45, it will be appreciated that the same procedure is used to implant a marker 50 whose wires are twisted together, or a marker 60 whose wires are welded together.

Referring first to FIG. 15, the barbs 46 at the forward end of the marker 40 are pressed together so that the free ends fit into the rearward end of the cannula 30. The marker 40 is advanced into the cannula. As the barbs 46 at the rearward end of the marker pass into the bore of the cannula 30, contact with the walls of the cannula force the trailing barbs into a substantially straight configuration. Though not shown in FIGS. 15–17, a plurality of markers 40 can be sequentially loaded into the cannula 30, as was described above with respect to the marker 10. A stylet 32 inserted into the rearward end of the cannula 30 is used to advance the marker or markers 40 forward through the cannula and to eject the marker(s) from the forward end of the cannula. As a marker 40 exits the forward end of the cannula 30, the barbs 46 spring outward, as shown in FIG. 17, piercing the target tissue 34 and anchoring the marker to the tissue.

It will be appreciated that a plurality of markers 40, 50, or 60 can be implanted in a single insertion, as explained above with respect to FIGS. 5–8, by sequentially loading a plurality of markers into a needle. If needed, to prevent the barbs of adjacent markers from riding up over one another and becoming entangled, adjacent markers can be separated by a small plug of a biodegradable material.

FIGS. 18–21 illustrate a device 70 for implanting markers 10 according to the present invention. The implantation device 70 includes a housing 72 formed from a pair of mating housing halves (only one of which is shown in the cutaway views of FIGS. 18–21). A hollow cannula 74 having a forward end 75 is mounted to the front 76 of the housing 72. A cantilevered latch arm 77, the end of which is seen in FIGS. 18–21, projects from the interior wall of the housing 72 in a direction which is generally perpendicular to the longitudinal axis of the device 70.

A trigger 78 is pivotably mounted on a pin 80 formed on the housing 72. A spring arm 82 is integrally molded with the trigger 78 and engages the housing 72 to bias the trigger 78 downward. Also molded integrally with the trigger 78 is an arm 84, which is attached to the trigger at its lower end by an integral hinge 86. The arm 84 has a free upper end 88.

A slide 90 is mounted within the housing 72 for linear movement along the longitudinal axis of the device. A stylet 92 extends forward from the slide 90 and is telescopically received within the hollow cannula 74. A coil spring 93 biases the slide rearward within the housing 72. A plurality of ratchet teeth 94, 96 are formed on the lower surface of the slide 90. The distance between the crests of adjacent ratchet teeth 94, 96 is equal to the length of a marker 10 in its uncoiled state. The upper end 88 of the arm 84 engages the ratchet teeth 94, 96 and prevents the slide 90 from moving rearward under the force of the spring 93.

Figure 18:
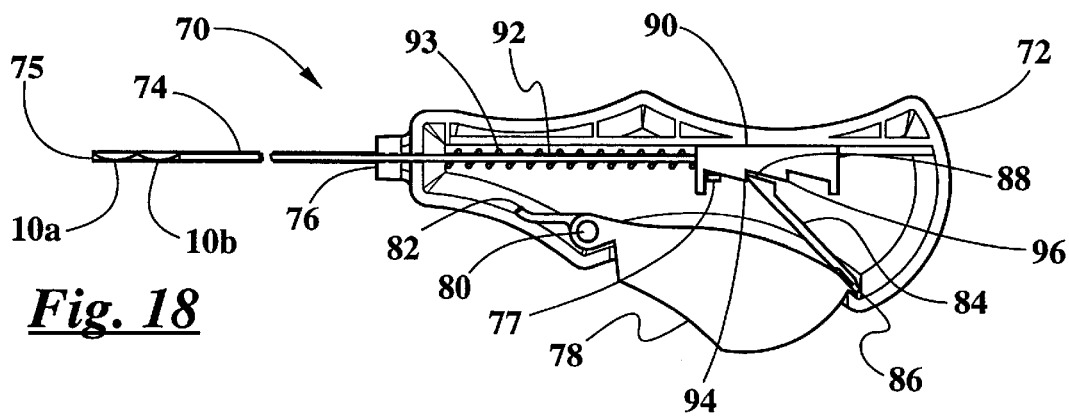
FIGS. 18–21 illustrate an apparatus and method for implanting the markers of FIG. 9, where

The deployment sequence by which two markers 10a, 10b are implanted will now be explained with reference to FIGS. 18–21. Referring first to FIG. 18, the two markers 10a, 10b are mounted within the forward end of the hollow cannula 74. The shape memory of the markers 10a, 10b causes them to assume a slightly bowed configuration, which creates sufficient friction with the interior walls of the cannula 74 to prevent the markers from sliding out of the forward end 75 of the cannula. The slide 90 is in its full rearward position, the latch arm 77 of the housing 72 resting in front of the first ratchet tooth 94. The upper end 88 of the arm 84 engages the trailing face of the first ratchet tooth 94.

Figure 19:
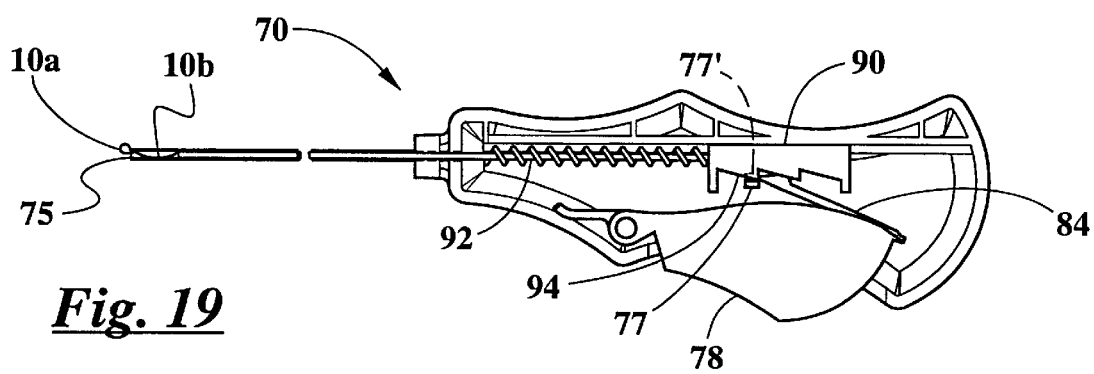

In FIG. 19 the trigger 78 has been depressed. The rotation of the trigger 78 causes the arm 84 to move forward to advance the slide 90. The latch arm 77 is deflected downward from its original position (shown in dashed lines 77') as the first ratchet tooth 94 advances over it. As the slide 90 advances, the stylet 92 pushes on the rearward marker 10b, which in turn pushes the front marker 10a out of the forward end 75 of the cannula 74.

Figure 20:
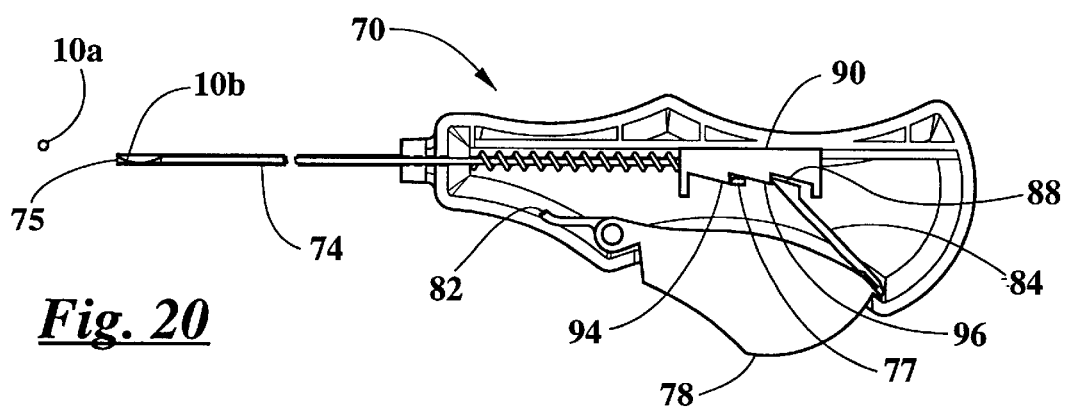

In FIG. 20 the trigger 78 has been released. The spring arm 82 pivots the trigger 78 downward, retracting the arm 84. The latch arm 77 of the housing engages the trailing edge of the front ratchet tooth 94 of the slide 90 to prevent the slide from moving rearward. The upper end 88 of the arm 84 now engages the trailing edge of the second ratchet tooth 96 of the slide 90. As can also be seen in FIG. 20, the first marker 10a assumes its helical shape memory upon being exposed to the body temperature of the target tissue.

Figure 21:
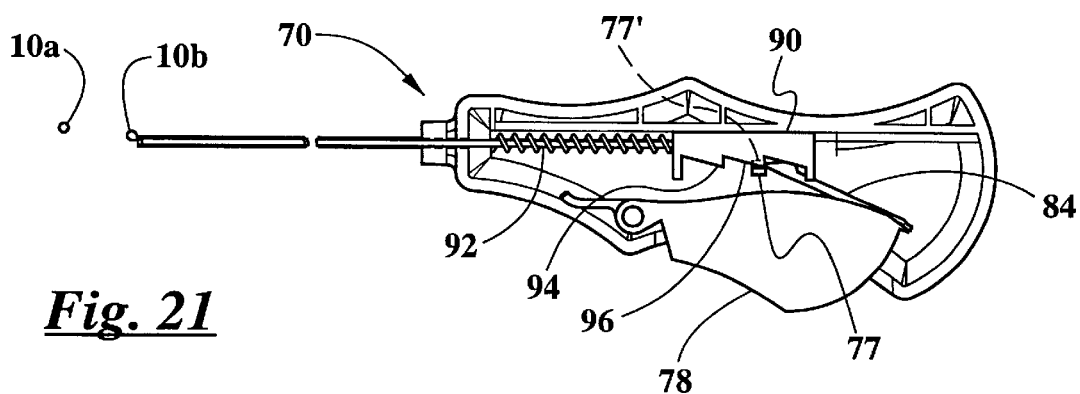

At this point, the instrument 70 can be repositioned to bring the forward end 75 of the cannula 74 into position adjacent a second target site. The trigger 78 is then depressed again, as shown in FIG. 21, causing the arm 84 to advance the slide 90. As the slide 90 advances, the stylet 92 forces the second marker 10b out of the forward end 75 of the cannula 74. The latch arm 77 is deflected downward again from its original position (shown in dashed lines 77') as the second ratchet tooth 96 passes. The latch arm 77 then springs upward as the second ratchet tooth 96 clears the latch arm to engage the trailing edge of the second ratchet tooth.

While the device 70 of FIGS. 18–21 is designed to implant two markers 10, it will be appreciated that the device can easily be modified to implant a greater or lesser number of markers by providing a longer or shorter slide with a greater or lesser number of ratchet teeth.

A feature common to all of the markers hereinabove described is that, once deployed within the target tissue, all of the markers are mechanically self-anchoring within the target tissue without the need for intervention by the physician. This feature provides the advantages that the implantation procedure is simplified, and the possibility is reduced that an omission by the physician or a mechanical malfunction of the marker will result in a marker migrating from its intended location or accidentally causing injury to the patient.

Finally, it will be understood that the preferred embodiment has been disclosed by way of example, and that other modifications may occur to those skilled in the art without departing from the scope and spirit of the appended claims.

What is claimed is:

1. A marker for inserting by a physician through a lumen of a hollow needle to a target site within the tissues of a patient to facilitate locating the target site at a later time, said marker being capable of assuming an essentially linear configuration for passage through said hollow needle, and said marker comprising means for anchoring itself to said tissues of said patient without intervention by said physician, wherein said marker comprises at least two wires having central portions which are fastened together, said at least two wires each having at least two free ends forming barbs for anchoring said marker within said tissues of said patient.

2. The marker of claim 1, wherein said marker further comprises a tubular body portion, and wherein said central portions of said at least two wires are anchored within said tubular body portion with said free ends extending from said tubular body portion to form said barbs.

3. The marker of claim 1, wherein said central portions of said at least two wires are twisted together.

4. The marker of claim 1, wherein said central portions of said at least two wires are bonded together.

5. The marker of claim 4, wherein said central portions of said at least two wires are welded together.

6. The marker of claim 4, wherein said central portions of said at least two wires are adhesively bonded together.

7. A method for implanting a plurality of markers within the tissues of a patient, comprising the steps of:

providing an elongated hollow needle in which a plurality of markers are sequentially loaded, said elongated hollow needle defining a longitudinal axis;

inserting a forward end of said elongated hollow needle into the tissues of a patient and advancing said forward end of said needle to a first target location;

discharging a first one of said plurality of markers from said forward end of said hollow needle in a direction substantially parallel to said longitudinal axis of said elongated hollow needle and into the tissues of said patient;

relocating said forward end of said hollow needle to a second target location;

discharging a second one of said plurality of markers from said forward end of said hollow needle in a direction substantially parallel to said longitudinal axis of said elongated hollow needle and into the tissues of said patient.

8. The method of claim 7, wherein said steps of discharging said first one and said second one of said plurality of markers from said forward end of said hollow needle comprise the steps of:

advancing a stylet forward within said hollow needle to push a rearmost one of said plurality of sequentially loaded markers so as to cause said first one and said second one of said markers to be discharged from said forward end of said needle.

9. An apparatus for delivering a plurality of implants to target locations within the tissues of a patient, comprising:

a housing;

an elongated hollow cannula mounted to said housing, said cannula having a longitudinal axis, and said cannula being configured to receive said plurality of implants within a forward end thereof, each of said implants having a length when disposed within said forward end of said cannula;

a slide mounted to said housing for movement in a direction generally parallel to said longitudinal axis of said cannula, said slide having a rearmost position;

a stylet telescopically received within said cannula and having a forward end and a rearward end mounted to said slide, said stylet having a length such as will cause said forward end of said stylet to bear against a rearward portion of the rearmost of said plurality of implants when said slide is in said rearmost position;

a trigger; and means operatively associated with said trigger and operative upon actuation of said trigger for advancing said slide and said stylet attached thereto by a distance equal to said length of each of said implants, whereby actuation of said trigger causes a single one of said plurality of implants to be ejected from said forward end of said cannula in a direction substantially parallel to said longitudinal axis of said cannula.

10. The apparatus of claim 9, wherein said means operatively associated with said trigger for advancing said slide comprises an arm attached to said trigger which engages a plurality of ratchet teeth on said slide.

11. The apparatus of claim 10, wherein an adjacent pair of said plurality of ratchet teeth is spaced apart by a distance equal to said length of each of said implants.

* * * * *